US006731967B1

(12) United States Patent
Turcott

(10) Patent No.: US 6,731,967 B1
(45) Date of Patent: May 4, 2004

(54) METHODS AND DEVICES FOR VASCULAR PLETHYSMOGRAPHY VIA MODULATION OF SOURCE INTENSITY

(75) Inventor: Robert Turcott, Menlo Park, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 470 days.

(21) Appl. No.: 09/907,349

(22) Filed: Jul. 16, 2001

(51) Int. Cl.[7] .................................. A61B 5/05
(52) U.S. Cl. .................. 600/407; 600/480; 600/485; 600/500; 600/473; 600/475; 600/477
(58) Field of Search .................. 600/407, 474, 600/478, 479, 480, 485, 486, 493, 500, 501, 502, 503, 504, 507, 508, 472, 473, 475, 476, 477, 428; 128/898

(56) References Cited

U.S. PATENT DOCUMENTS 5,218,207 A * 6/1993 Rosenthal .................. 600/473
5,370,114 A * 12/1994 Wong et al. ............... 600/473
5,590,652 A * 1/1997 Inai .......................... 600/479
6,561,984 B1 * 5/2003 Turcott ...................... 600/485
6,575,912 B1 * 6/2003 Turcott ...................... 600/485

* cited by examiner

Primary Examiner—Henry Bennett
Assistant Examiner—Fadi H. Dahbour
(74) Attorney, Agent, or Firm—Steven M. Mitchell

(57) ABSTRACT

A time-varying modulating signal is used as a plethysmography signal, rather than a time-varying detected optical power. The time-varying detected optical power is used (e.g., in a feedback loop) to adjust the source intensity. Light is transmitted from a light source, wherein an intensity of the transmitted light is based on a light control signal. A portion of the light transmitted from the light source is received at a light detector, the portion having an associated detected light intensity. A feedback signal is produced based the portion of light received at the light detector, the feedback signal indicative of the detected light intensity. The feedback signal is compared to a reference signal to produce a comparison signal. The light control signal is then adjusted based on the comparison signal, wherein at least one of the comparison signal and the light control signal is representative of volume changes in blood vessels.

48 Claims, 13 Drawing Sheets

METHODS AND DEVICES FOR VASCULAR PLETHYSMOGRAPHY VIA MODULATION OF SOURCE INTENSITY

BACKGROUND OF THE INVENTION

1. Field of the Invention

The present invention relates generally to non-invasive and implantable (i.e., invasive) plethysmography methods and devices. The present invention more particularly relates to methods and devices for monitoring volume changes in a limb or tissue segment of a patient. The present invention also relates to methods and devices that calculate blood oxygenation levels.

2. Background Art

Plethysmography is a generic term referring to a variety of techniques for monitoring volume changes, for example, volume changes of the lungs due to respiration, or of blood vessels of a limb or tissue segment. When applied to measurements of blood volume, changes occur in a pulsatile manner with each beat of the heart as blood flows in and out of a portion of the body. The study of vascular activity by fluid displacement methods dates back to at least 1890. More contemporary techniques include strain gauge, pneumatic, impedance, doppler, and photoelectric plethysmography. A plethysmography device produces a waveform that is similar to an arterial pressure waveform. The waveform is useful in measuring pulse velocity and indicating arterial obstructions.

FIG. 1 illustrates an exemplary plethysmograph 100, which includes a waveform 102 produced by a plethysmography device. For timing reference, an electrocardiogram (ECG) signal 104 is illustrated. Waveform 102 provides a measure of the volume of the arterial vasculature. A measure of arterial pulse amplitude is derived from it. A few tens to a few hundreds of milliseconds after the QRS complex, the plethysmography voltage reaches a minimum and starts to increase. This is due to the increasing blood volume in the arterioles as the systolic pulse reaches the periphery. The delay is influenced by the distance that the sensor is placed from the heart. It requires approximately 100 msec for the waveform to reach its maximum. The excursion from minimum to maximum represents the arterial pulse amplitude. During diastole, the recoil of the elastic arterial vessels continues to force blood through the capillaries, so that blood flows through the capillary bed throughout the entire cardiac cycle.

A photoplethysmography device (PPG) (also called a pseudoplethysmography or photoelectric plethysmography device) includes a light detector and a light source. The PPG utilizes the transmission or reflection of light to demonstrate the changes in blood perfusion. Such devices might be used in the cardiology department or intensive care department of a hospital or in a clinic for diagnostic purposes related to vascular surgery. A photoplethysmography device is also referred to, herein, simply as a plethysmography device.

An exemplary circuit 200A for a conventional photoplethysmography device is shown in FIG. 2A. An exemplary mechanical arrangement 200B for a conventional photoplethysmography device is shown in FIG. 2B. In these examples, the light source is a light-emitting diode (LED) 202, although in alternative models an incandescent lamp can be used as the light source. The light detector in this example is a photoresistor 204 excited by a constant current source. Changes in light intensity cause proportional changes in the resistance of the photoresistor. Since the current through the photoresistor is constant in this example, the resistance changes produce varying analog voltage ($V_{out\_analog}$) at the output terminal. In order to be useful, this varying analog voltage ($V_{out\_analog}$) typically must be converted to a digital signal ($V_{out\_digital}$) using an analog to digital converter (A/D) 206. Other known light detectors include photo diodes, photo transistors, photo darlingtons and avalanche photo diodes. Light detectors are often also referred to as photo detectors or photo cells.

Light may be transmitted through a capillary bed such as in an ear lobe or finger tip. As arterial pulsations fill the capillary bed the changes in volume of the blood vessels modify the absorption, reflection and scattering of the light. Stated another way, an arterial pulse in, for example, a finger tip, or ear lobe, causes blood volume to change, thereby changing the optical density of the tissue. Therefore, the arterial pulse modulates the intensity of the light passing through the tissue. Light from LED 202 is reflected into photoresistor 204 by scattering and/or by direct reflection from an underlying bone structure. Such a PPG does not indicate "calibratable" value changes. Thus, its usefulness is generally limited to pulse-velocity measurements, determination of heart rate, and an indication of the existence of a pulse (e.g., in a finger). Additionally, a conventional PPG provides a poor measure of changes in volume and is very sensitive to motion artifacts.

It is noted that photoplethysmography devices may operate in either a transmission configuration or a reflection configuration. In the transmission configuration, the light source (e.g., LED 202) and the photodetector (e.g., 204) face one another and a segment of the body (e.g., a finger or earlobe) is interposed between the source and detector. In the reflection configuration, the light source (e.g., LED 202) and photodetector (e.g., 204) are mounted adjacent to one another, e.g., on the surface of the body, as shown in FIG. 2B. If the photoplethysmography device is incorporated into an implantable cardioverter defibrillator (ICD) or other implantable therapy device or monitor, and thus implanted, then the light source (e.g., LED 202) and light detector (e.g., 204) can be mounted adjacent to one another on the housing (e.g., can) or header of the ICD, as disclosed in U.S. patent application Ser. No. 09/543,214, entitled "Extravascular Hemodynamic Sensor", filed Apr. 5, 2000, which is incorporated herein by reference in its entirety.

In a conventional photoplethysmography device (e.g., 100A), a constant average optical power is delivered by the optical source (e.g., LED 202) and plethysmograph information (e.g., waveform 102 shown in FIG. 1) is determined based on time varying optical power incident on the detector (e.g., photoresistor 204). This approach is not optimal for many reasons, some of which are discussed above and others of which are discussed below.

First, providing a constant average optical power does not allow for power consumption to be minimized. This may not be a concern if the plethysmography device is a non-invasive device, and thus, can receive power from an relatively inexpensive and inexhaustible power supply. However, if the plethysmography device is an implantable device (or part of an implantable device), as is the case in many embodiments of the present invention, the device is likely powered by a battery that is not easily accessible. For example, if the plethysmograph is incorporated into an ICD, pacemaker, or other implantable therapy device or monitor, then the battery of the device could be used to power components (e.g., LEDs, amplifiers) of the plethysmography device. Typically, invasive surgery is required to replace the ICD or pacemaker when its battery nears depletion.

Accordingly, there is a need to minimize power consumption of the components of the plethysmography device. This holds true for any implantable plethysmography device, whether or not it is incorporated into an ICD or pacemaker.

Second, the dynamic range (e.g., linear range) of a photodiode, or any other type of photoresistor or photodetector, is limited. The upper limit is usually a function of the saturation point of the detector and/or detector amplifiers. The lower limit is typically a function of environmental and/or circuit noise. When any of these components are operating outside of its dynamic range, the accuracy and integrity of the information being obtained (e.g., plethysmography waveform 102) is adversely affected. Accordingly, there is a need to operate a plethysmography device within the dynamic range of its components. The criticality of this need is increased when the plethysmography device is an implantable device (or part of an implantable device). This is because, over time, the human body begins to encapsulate an implanted device with a fibrous capsule. Such a fibrous capsule can change the amount of light that reaches the detector of a plethysmography device. This can cause components (e.g., a photodiode and/or amplifier) to operate outside of their dynamic range, thereby adversely affecting the accuracy and integrity of the plethysmography information. This further increases the need to operate a plethysmography device within the range of its components. Accordingly, there is a need to compensate for the fibrous capsule that, slowly, over time, encapsulates an implanted plethysmography device.

Third, as mentioned above, the varying analog voltage output (e.g., $V_{out\_analog}$) of a conventional plethysmography device typically must be converted to a digital signal (e.g., $V_{out\_digital}$) using an analog to digital converted (e.g., A/D 106). Such an analog to digital convert consumes power to perform its conversion. As also mentioned above, minimizing power consumption is very important when the plethysmography device is implanted. Accordingly, it would be beneficial to avoid the necessity of an analog to digital converter, to thereby reduce power consumption.

BRIEF SUMMARY OF THE INVENTION

The present invention, which relates to monitoring volume changes in blood vessels, is directed towards methods for use with a medical device that includes a light source and a light detector. A time-varying modulating signal is used as a plethysmography signal, rather than a time-varying detected optical power. The time-varying detected optical power is used (e.g., in a feedback loop) to adjust the source intensity.

According to an embodiment of the present invention, light is transmitted from the light source. An intensity of the transmitted light is based on a light control signal. The light detector receives a portion of the light transmitted from the light source. The received portion has an associated detected light intensity. A feedback signal is produced based on the portion of light received at the light detector. The feedback signal is indicative of the detected light intensity. The feedback signal is compared to a reference signal to produce a comparison signal. The light control signal is adjusted based on the comparison signal. At least one of the comparison signal and the light control signal is representative of volume changes in blood vessels.

According to an embodiment of the present invention, the light control signal is adjusted to keep the detected light intensity of the portion of light received at the light detector relatively constant. An amplitude of the light control signal can be adjusted to keep the detected light intensity of the portion of light received at the light detector relatively constant. According to another embodiment of the present invention, a frequency of the light control signal is adjusted to keep the detected light intensity of the portion of light received at the light detector relatively constant. In another embodiment, a pulse width of the light control signal is adjusted to keep the detected light intensity of the portion of light received at the light detector relatively constant.

According to an embodiment of the present invention, the light control signal is adjusted to minimize a difference between the feedback signal and a reference signal. The amplitude, frequency and/or pulse widths of the light control signal can be adjusted to minimize the difference between the feedback signal and the reference signal.

In an embodiment of the present invention, the light control signal includes a digital signal, and the light source includes a plurality of LEDs, each of which is on or off based on the digital signal. The digital signal is adjusted to minimize a difference between the feedback signal and the reference signal, or to keep the detected light intensity of the portion of light received at the light detector relatively constant.

The light source can transmit light of more than one wavelength. For example, in an embodiment of the present invention the light source transmits light having a first wavelength and light having a second wavelength. An intensity of the transmitted light is based on a first light control signal and a second light control signal. The light detector receives a portion of the light having the first wavelength and a portion of the light having the second wavelength transmitted from the light source. Each portion has an associated detected light intensity. A first feedback signal is produced based on the portion of light having the first wavelength. A second feedback signal is produced based on the portion of light having the second wavelength. Each feedback signal is indicative of the associated detected light intensity. The first feedback signal is compared to a reference signal to produce a first comparison signal. The second feedback signal is compared to a reference signal to produce a second comparison signal. The first and second reference signals may or may not be the same signal. The first and second light control signals are adjusted, respectively, based on the first and second comparison signals. The first and second comparison signals are representative of volume changes in blood vessels. In an embodiment of the present invention, blood oxygenation levels are calculated based on the first and second comparison signals. In an embodiment, the first wavelength is within the red visible light spectrum, and the second wavelength is within the infrared or near infrared light spectrum.

The devices of the present invention can be non-invasive or implantable. An embodiment of the present invention is directed to an implantable device for monitoring volume changes in blood vessels. The implantable device includes a light source adapted to transmit light. The implantable device also includes a light detector adapted to receive a portion of the light transmitted from the light source. The portion of light received at the light detector has an associated detected light intensity. A light controller of the implantable device is adapted to adjust an intensity of the transmitted light based on the detected light intensity. The device also determines volume changes in blood vessels based a signal produced by the light controller, wherein the signal is proportional the intensity of the transmitted light. The light source and the light detector can be located adjacent to one another on the can or header of the implantable device. The light controller is preferably located within a sealed portion of the implantable device.

BRIEF DESCRIPTION OF THE DRAWINGS/ FIGURES

Further features and advantages of the present invention may be more readily understood by reference to the following description taken in conjunction with the accompanying drawings. The left-most digit(s) of a reference number identifies the drawing in which the reference number first appears.

DETAILED DESCRIPTION OF THE INVENTION

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

I. Overview of Present Invention

Instead of providing a constant source of optical power (e.g., a light source having a constant intensity) and using a time-varying detected signal as the plethysmography signal (i.e., the information signal), the present invention adjusts the source of optical power such that a relatively constant average light intensity is detected at a light detector. The time-varying modulating signal (i.e., that controls the source power) is used as the plethysmography signal (i.e., the information signal), rather than the time-varying detected optical power. The time-varying detected optical power is used (e.g., in a feedback loop) to adjust the source intensity.

In many embodiments of the present invention a set point (e.g., a reference voltage signal) is established, and any deviation of the detected light away from the set point induces an increase or decrease of the source intensity that acts in a direction opposite the deviation of the detected light. Specifically, if the detected light moves above (i.e., higher than) the set point, then the source intensity is decreased. Conversely, if the detected light moves below (i.e., lower than) the set point, then the source intensity is increased. According to specific embodiments, the amount the source intensity is adjusted is proportional to the amount of the excursion of the detected light from the set point. In embodiments of the present invention, the information signal of interest is taken from the light source. More particularly the information signal of interest is taken from the control signal or a comparison signal the controls the light source, rather than from the light detector, as in the conventional approaches.

Figure 3:
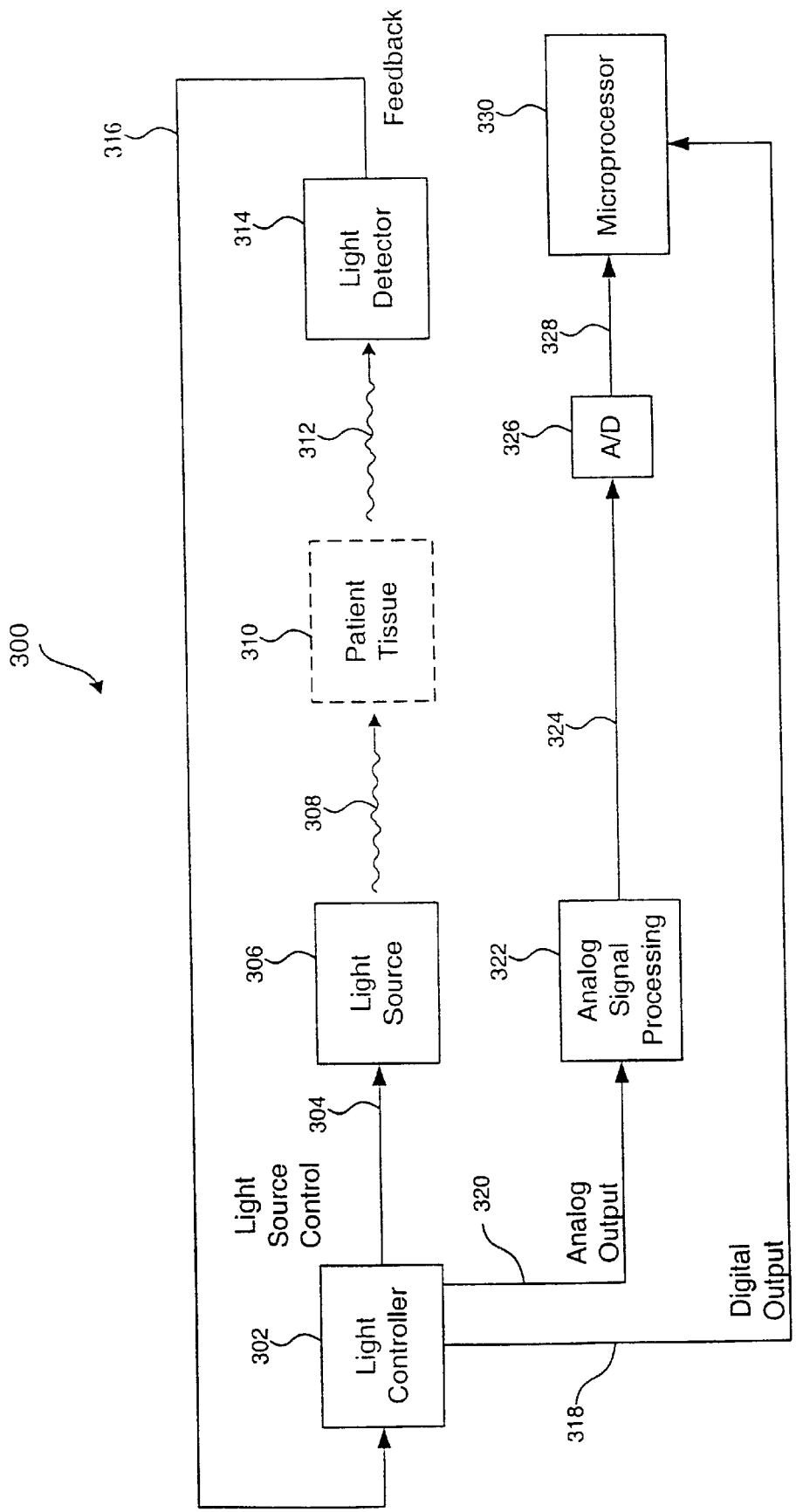
FIG. 3 illustrates an overview of a photoplethysmography device according to an embodiment of the present invention.

FIG. 3 includes a block diagram 300 that provides an overview of the present invention. A light controller 302 produces a light control signal 304 that drives a light source 306. Light source 306 outputs a transmit light signal 308 based on light control signal 304. Light signal 308 is transmitted through and/or reflected by (depending on the embodiment) patient tissue 310. A receive light signal 312 is received by a light detector 314.

Light detector 314 provides a feedback signal 316 to light controller 302. Light controller 302 adjusts light control signal 304, based on a difference between feedback signal 316 and a reference signal, such that a relatively constant average light intensity is detected by light detector 314. Stated another way, light controller 302 adjusts light control signal 304, based on a difference between feedback signal 316 and a reference signal, such that the difference between feedback signal 316 and the reference signal is minimized.

In the present invention, a time-varying modulating signal of light controller 302 is used as (or to produce) the plethysmography signal (i.e., the information signal), rather than the time-varying detected optical power. In specific embodiments of the present invention, one or more digital output signals 318, which are digitally encoded information signals, are provided from light controller 302 to a microprocessor 330.

Alternatively and/or additionally, depending on the embodiment, an analog output signal 320 is provided from the light controller 302. Analog output signal 320, which is an analog encoded information signal, is preferably filtered and amplified by analog signal processor block 322. A filtered and amplified signal 324 is then provided to an analog to digital converted (A/D) 326, which provides a digital encoded information signal 328 to microprocessor 330.

Microprocessor 330 analyzes the encoded information signals (e.g., 318 and/or 328). Microprocessor 330 can, for example, produce a plethysmography waveform based on the encoded information signals. Additionally or alternatively, microprocessor 330 can determine arterial pulse amplitudes based on maximum and minimum values deciphered from the encoded information signals over durations of cardiac cycles, or based on other analysis of the information signal. Microprocessor 330 can also use the encoded information signals to optimize cardiac pacing parameters using optimization algorithms. Exemplary optimization algorithms are disclosed in U.S. patent application Ser. No. 09/759,395, entitled "Methods, Systems and Devices for Optimizing Cardiac Pacing Parameters", filed Jan. 12, 2001, and U.S. patent application Ser. No. 09/780,735, entitled "Methods, Systems and Devices for Optimizing Cardiac Pacing Parameters Using Evolutionary Algorithms", filed Feb. 9, 2001, each of which is assigned to the same assignee as the present invention, and each of which is incorporated herein by reference in its entirety.

1. Light Source

Figure 4B:
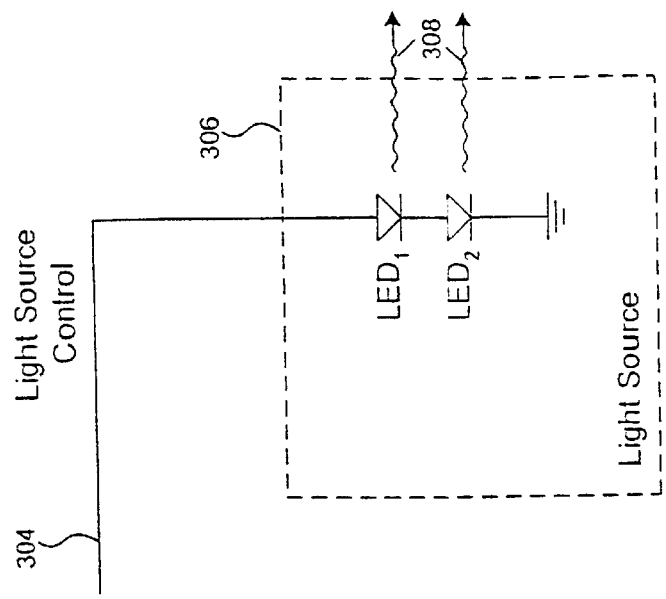
FIGS. 4A and 4B illustrate exemplary light sources for use in the embodiments of the present invention.
Figure 4A:
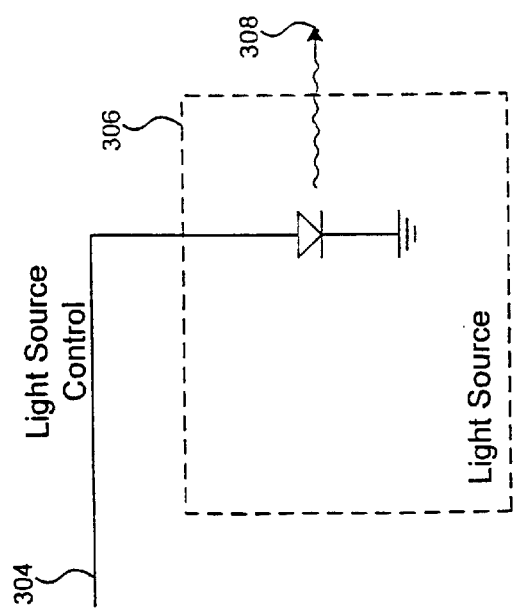

FIGS. 4A and 4B illustrate exemplary light sources for use in the embodiments of the present invention. Referring first to FIG. 4A, exemplary light source 306 includes a single LED that produces light signal 308. The LED can be, for example, a model L53SRC/F red LED, or a model L53F3C infrared LED, both manufactured by Kingbright Corporation, City of Industry, Calif. Referring to FIG. 4B, a series of LEDs (e.g., $LED_1$ and $LED_2$) can be used to increase the amount of optical power (from a given amount of electrical power, e.g., battery power) in light signal 308. Separate LEDs can be used. Alternatively, dual emitter combination LEDs can be used, such as model DLED-660/905-LL5-2, manufactured by UDT Sensors, Inc., Hawthorne, Calif. In each of the embodiments, light source 306 is driven by light control signal 304 and outputs transmit light signal 308. Alternative light sources 306 are disclosed in the various embodiments of the present invention discussed below. One of ordinary skill in the art will appreciate that the use of other LEDs, and other light sources (e.g., a laser diode), are within the spirit and scope of the present invention. Depending on the embodiment, light source 306 may or may not include additional elements that are, for example, used to maintain a relatively constant current across an LED. However, these additional elements can be considered part of light controller 302.

2. Light Detector

Figure 5:
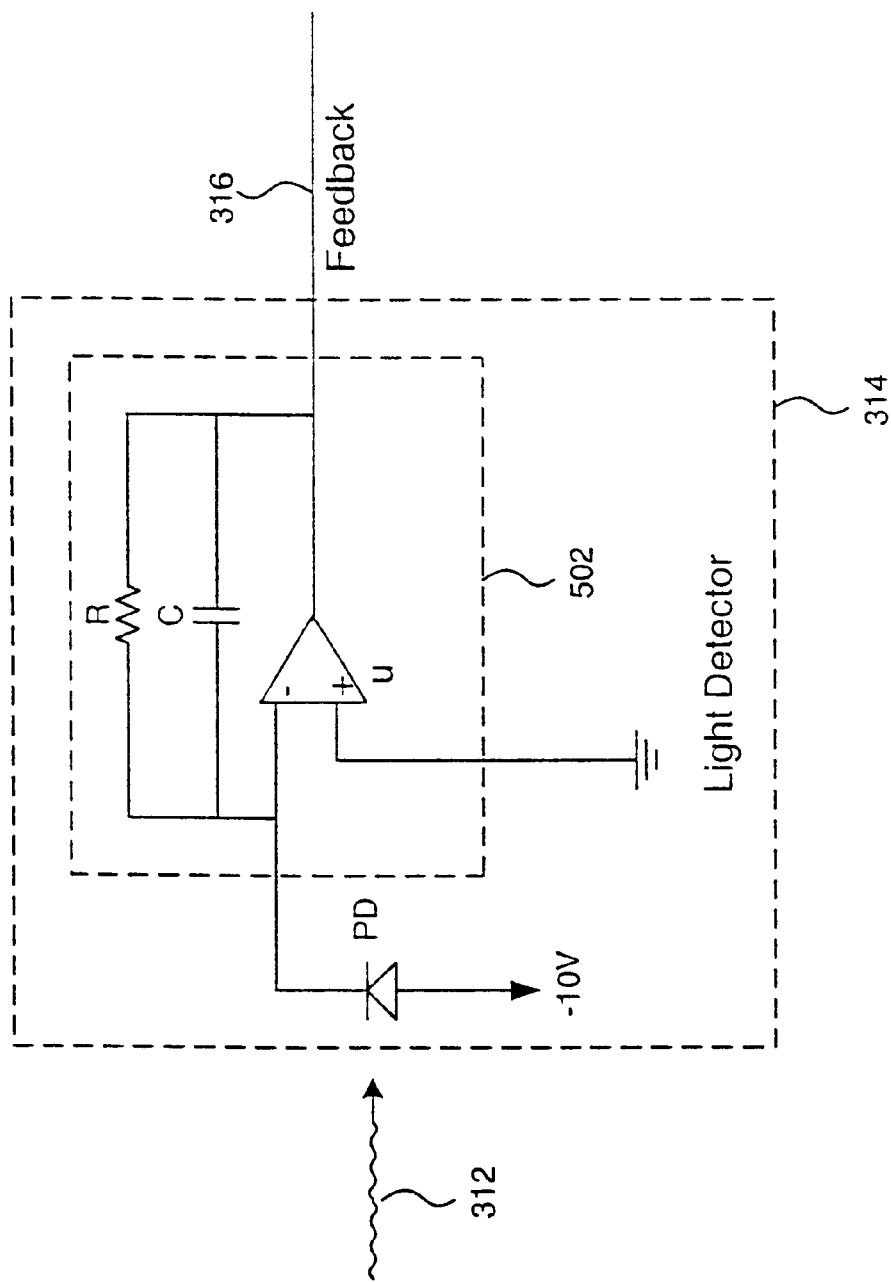
FIG. 5 illustrates an exemplary light detector for use in the embodiments of the present invention.

FIG. 5 illustrates and exemplary light detector for use in the embodiments of the present invention. Referring to FIG. 5, exemplary light detector 314 includes a photodiode PD operated in a current sensing photoconductive mode feeding a transimpedance amplifier 502. Photodiode PD can be, for example, a model PIN-4.0-LLS, manufactured by UDI Sensors, Inc. Transimpedance amplifier 502 includes a resistor R, a capacitor C and an operation amplifier U, such as model ALD1701, manufactured by Advanced Linear Devices, Inc., Sunnyvale, Calif. Amplifier 502, including the RC circuit, performs low pass filtering, anti-alias filtering, and provides gain. One of ordinary skill in the art will appreciate that a photodiode PD can alternatively be operated in a voltage sensing configuration.

Alternative light detectors 314 arc disclosed in the various embodiments of the present invention discussed below. One of ordinary skill in the art will appreciate that the use of other photodiodes (e.g., an avalanche photodiode) and other light detectors (e.g., a photo resistor, a photo darlington, a photo transistor), are within the spirit and scope of the present invention. One of ordinary skill in the art will also appreciate that other amplifier configurations (e.g., an integrator amplifier, a transistor based amplifier) can be used in place of transimpedance amplifier 502 shown in FIG. 5. An integrated photodiode/amplifier (e.g., a Burr-Brown OPT101) can also be used.

Below is a discussion of specific embodiments of the present invention. In the drawings, like reference numbers indicate identical or functionally similar elements. Additionally, many of the drawings highlight features and elements that differ from previously discussed embodiments. Accordingly, where features and elements of drawings are identical to or similar to those of previous drawings, these identical or similar features may be left out of the drawings. For example, FIGS. 6, 7, 8 and 9 do not explicitly show light detector 314, because the embodiments disclosed in these figures are not dependent on the exact implementation of light detector 314.

II. Adjust Amplitude

Figure 6:
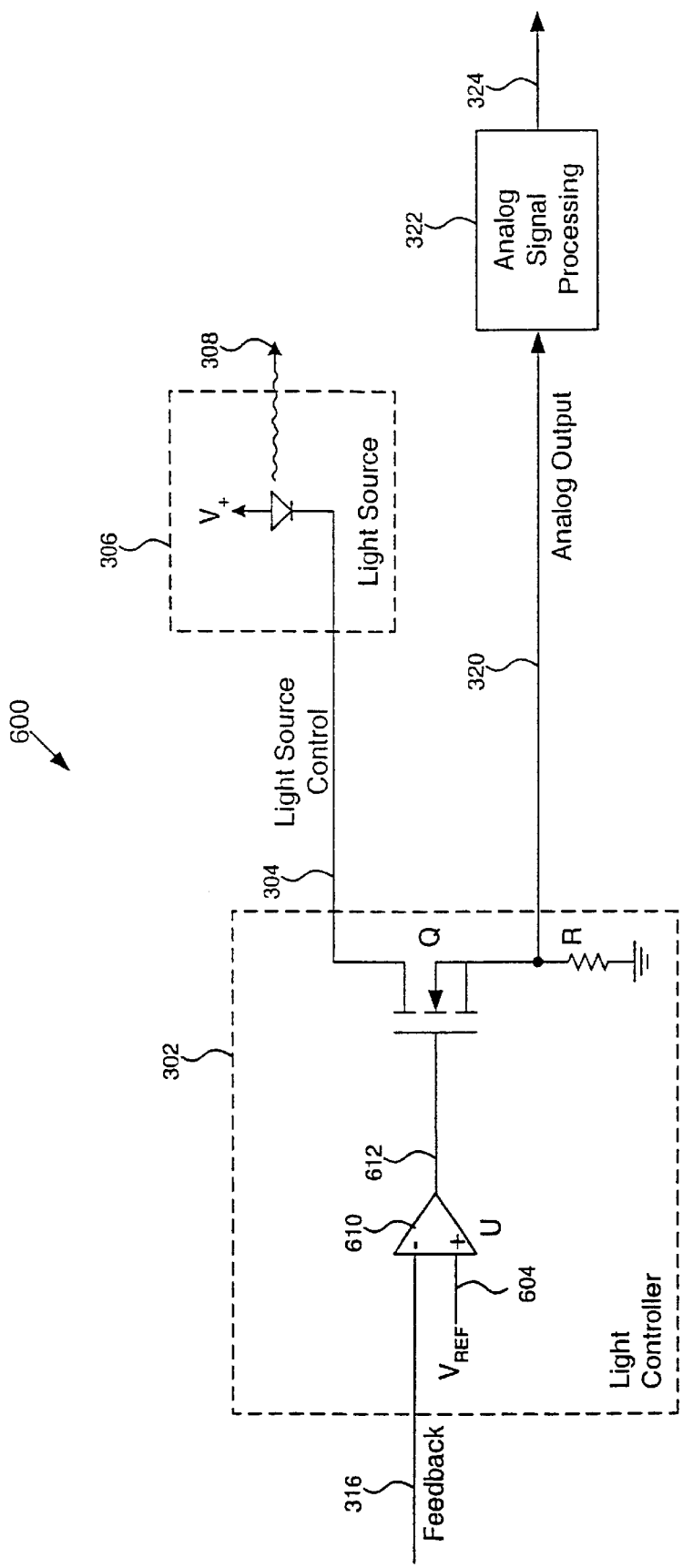
FIG. 6 illustrates a photoplethysmography device that adjusts a current or voltage amplitude that drives a light source, according to an embodiment of the present invention.

According to an embodiment of the present invention, an amplitude of the current or voltage that drives a light source of a photoplethysmography device is adjusted so that a relatively constant average light intensity is detected at a light detector of the device. FIG. 6 shows an exemplary diagram of a device 600 that can be used to implement this embodiment of the present invention.

Device 600 includes a light controller 302 that outputs a light control signal 304 that drives a light source 306. In this embodiment, light control signal 304 is an analog voltage or current signal having a variable voltage or current amplitude. More specifically, in this embodiment the amplitude of the light control signal 304 is adjusted (i.e., increased or decreased) by light controller 302, based on a difference between feedback signal 316 and a reference signal so that a relatively constant average light intensity is detected by light detector 314. Stated another way, light controller 316 adjusts the amplitude of light control signal 304, based on a difference between feedback signal 316 and a reference signal, such that the difference between feedback signal 316 and the reference signal is minimized.

In this embodiment, light controller 302 includes a comparator 610 (e.g., operation amplifier U), which compares feedback signal 316 to a fixed reference voltage signal 604 (e.g., 1.2 volts). The term "comparator" is used herein to refer to a device that performs a comparison between two input signals and generates an analog or digital (e.g., binary) output based on the results of the comparison. In this embodiment, comparator 610 produces an analog output based on the comparison. Light controller 302 also includes a transistor Q (e.g., a MOSFET transistor as shown). Transistor Q is controlled by an output 612 (also referred to as comparison signal 612) of comparator 610. More specifically, transistor Q is turned on by an amount proportional to a difference between feedback signal 316 and fixed reference voltage signal 604. One of ordinary skill in the art will appreciate that various types of transistors, and/or various other types of current control circuits, can be used while still being within the spirit and scope of the present invention.

In this embodiment, a modulated LED current, carrying the plethysmograph information, is sensed using a sense resistor R. More specifically, the information signal of interest, analog output 320 (which is the voltage across resistor R), is proportional to the LED current. As shown in FIG. 6, this signal 320 can be provided to analog signal processor 322. Filtered and amplified signal 324 can then be provided to A/D 326, which provides a digital encoded information signal 328 to microprocessor 330 (as shown in FIG. 3).

Microprocessor 330 analyzes encoded information signal 328. For example, microprocessor 330 can produce a plethysmography waveform based on the encoded information signals. Additionally or alternatively, microprocessor 330 can determine arterial pulse amplitudes, e.g., based on maximum and minimum values deciphered from the encoded information signals over durations of cardiac cycles. Microprocessor 330 can also use the encoded information signals to optimize cardiac pacing parameters using optimization algorithms.

III. Adjust Pulse Frequency

Figure 7:
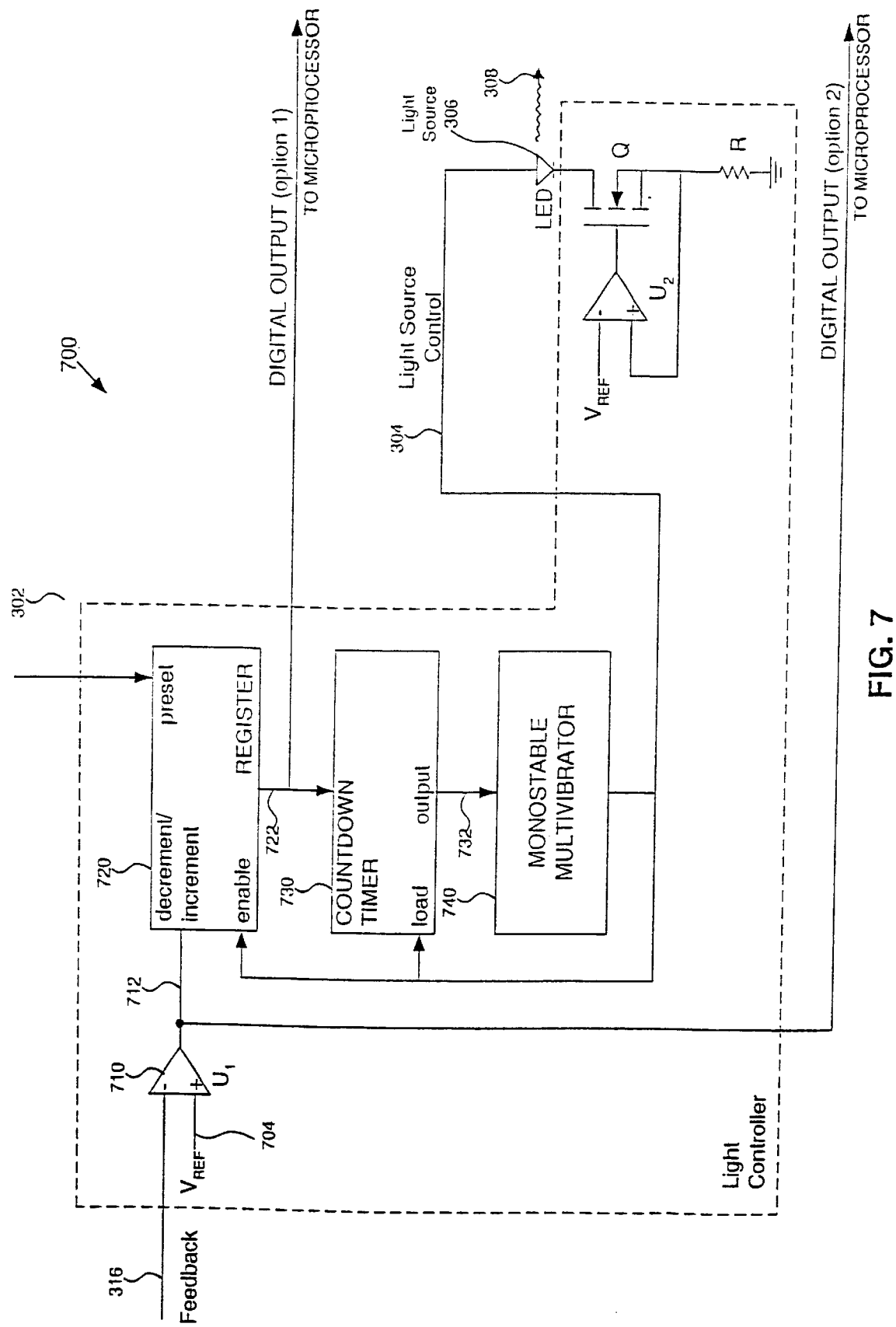
FIG. 7 illustrates a photoplethysmography device that adjusts a frequency of a pulse train that drives a light source, according to an embodiment of the present invention.

According to another embodiment of the present invention, the frequency of a pulse train that drives a light source of a photoplethysmography device is adjusted so that a relatively constant average light intensity is detected at a light detector of the device. FIG. 7 shows an exemplary block diagram of a device 700 that can be used to implement this embodiment of the present invention.

Device 700 includes a light controller 302 which outputs a light control signal 304 that drives a light source 306. In this embodiment, light control signal 304 is a train of pulses (i.e., a pulse train) having a constant amplitude and a variable frequency. More specifically, in this embodiment the frequency of the pulse train of light control signal 304 is adjusted (i.e., increased or decreased) by light controller 302, based on a difference between feedback signal 316 and a reference signal 704 so that a relatively constant average light intensity is detected by light detector 314. Stated another way, light controller 316 adjusts the frequency of light control signal 304, based on a difference between feedback signal 316 and a reference signal 704, such that the difference between feedback signal 316 and the reference signal 704 is minimized.

In this embodiment, light controller 302 includes a comparator 710, which compares feedback signal 316 to a fixed reference voltage signal 704 (e.g., 1.2 volts) to produce a comparison signal 712. Light controller 302 also includes a register 720 that can initially be preset to a convenient value (e.g., 200) that represents a predetermined duration (e.g., 2 milliseconds). When register 720 is enabled (e.g., via an enable input) by a pulse from a monostable multivibrator 740, register 720 is decremented or incremented depending on whether an output 712 of comparator 710 (i.e., comparison signal 712) is HIGH or LOW, respectively.

A pulse from monostable multivibrator 740 also causes the new value (i.e., the value produced by decrementing or incrementing a previous value) in register 720 to be loaded into a count-down timer 730 via register output line 722. When count-down timer 730 reaches zero, its output 732 causes a pulse to be generated by monostable multivibrator 740 (e.g., of duration 10 microseconds). Each output pulse, which is delivered to light source 306 as light control signal 304, causes an optical pulse to be generated by light source 306 and transmitted as transmit light signal 308.

Light source 306 includes an LED (or, e.g., an array of LEDs). Light controller 302 is shown as also having a circuit including an operation amplifier $U_2$, and transistor Q, and a resistor R. This circuit keeps the current across the LED constant when light control signal 304 is HIGH. Accordingly, this circuit can be considered part of light source 306, rather than part of light controller 302.

Preferably, the typical pulse rate of light source 306 is much greater than the frequency content of the plethysmography information, which is approximately 1–20 Hz. Accordingly, a convenient LED pulse rate is around 2 kHz (e.g., between 1.5 kHz and 2.5 kHz). One of ordinary skill in the art will appreciate that various other pulse rates can be used while still being within the spirit and scope of the present invention.

In this embodiment, the modulation of light source 306 carries the plethysmography information, and the modulation of light source 306 is encoded in digital signals. Hence, no analog to digital (A/D) conversion is necessary. The source modulation can be monitored in several different ways, some of which are discussed below. In each of these embodiments, it should be appreciated that the plethysmography information is obtained directly or indirectly from comparison signal 712.

In one embodiment (i.e., option 1), contents of register 320 are recorded, for example, by a microprocessor or microcontroller 330 (shown in FIG. 3). According to the Nyquist theorem, register 320 need only be sampled at twice the highest frequency of the signal of interest. Sampling the register at 60–100 Hz is convenient. Other embodiments include digital logic that retains a maximum and/or a minimum value of register 320 over the duration of a cardiac cycle. At the end of the cardiac cycle, the maximum and/or minimum value(s) represent the arterial pulse amplitude, and are transferred to the microprocessor or microcontroller 330. Microprocessor 330 then analyzes and utilizes encoded information signal 328, as discussed above.

In another embodiment (i.e., option 2), output 712 of comparator 710 (i.e., comparison signal 712) is sampled to produce a digital output. Because comparator 910 is a high gain amplifier configured without negative feedback, its output will be either a LOW or HIGH signal. That it, it is essentially a digital signal. This is an implementation of a well-known sigma-delta modulation technique, which relies on oversampling a signal (e.g., comparison signal 712, in this embodiment) to the point where a low resolution quantizer produces a sufficient representation of the signal. Comparison signal 712 should be sampled at a relatively high rate, e.g., at the same rate of the LED pulse drive.

IV. Adjust Pulse Width

Figure 8:
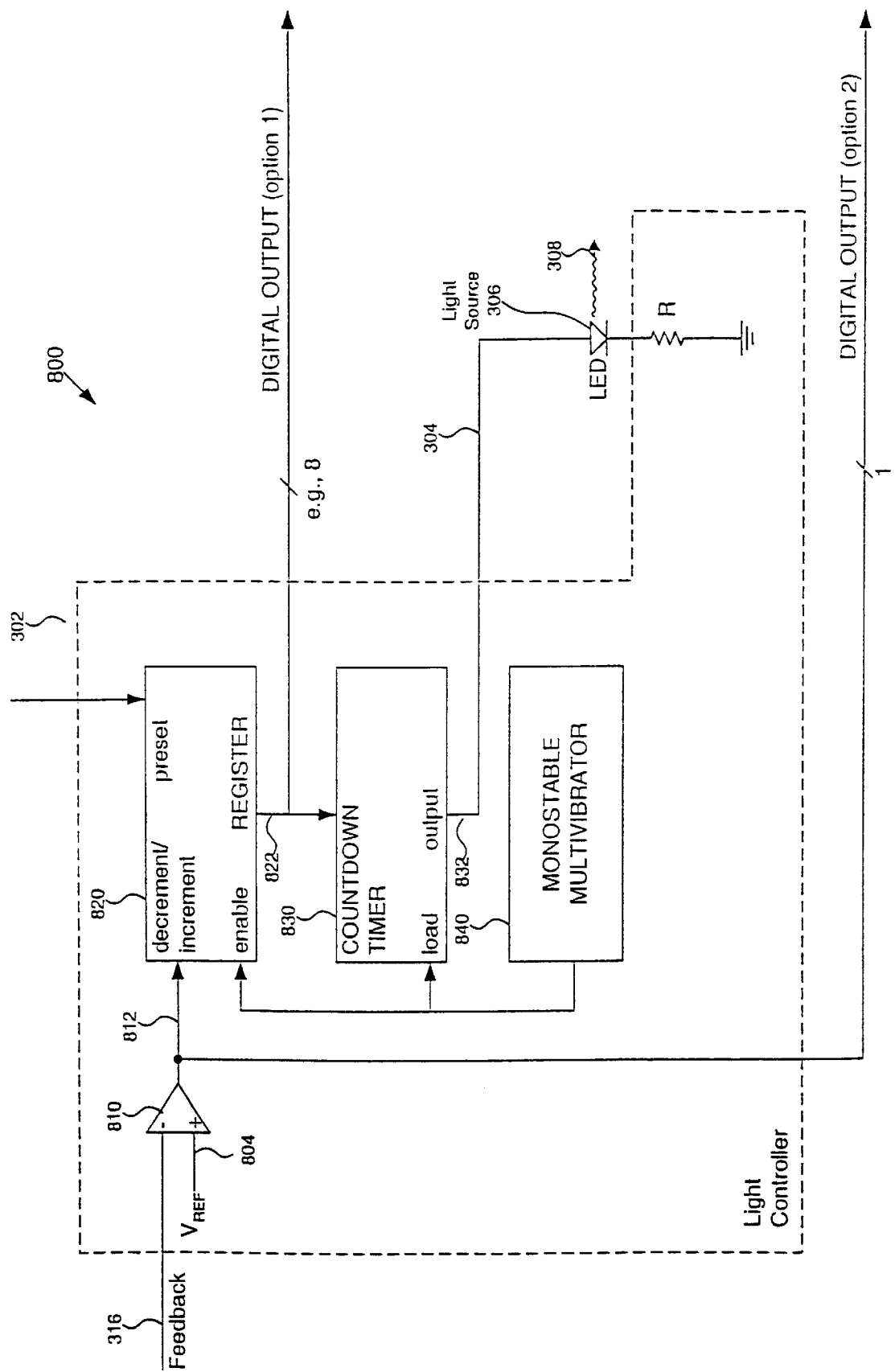
FIG. 8 illustrates a photoplethysmography device that adjusts pulse widths of pulses of a pulse train that drives a light source, according to an embodiment of the present invention.

According to another embodiment of the present invention, the pulse widths of pulses of a pulse train that drives a light source of a photoplethysmography device are adjusted so that a relatively constant average light intensity is detected at a light detector of the device. FIG. 8 shows an exemplary block diagram of a device 800 that can be used to implement this embodiment of the present invention.

In this embodiment, light source 306 (e.g., one or more LEDs) is pulsed with a fixed current and fixed frequency, but the duration of pulses are adjusted such that a relatively constant average light intensity is detected by light detector 302. More specifically, a difference between feedback signal 316 (from light detector 314) and a reference signal is used to increase or decrease the duration of pulses in the pulse train driving light source 306 so that a relatively constant average light intensity is detected by light detector 314. Stated another way, light controller 316 adjusts the duration of pulses of light control signal 304, based on a difference between feedback signal 316 and a reference signal 804, such that the difference between feedback signal 316 and the reference signal 804 is minimized.

In this embodiment, light controller 302 includes a comparator 810 that compares feedback signal 316 to a fixed reference voltage signal 804 (e.g., 1.2 volts). Light controller 302 also includes a register 820 that can initially be preset to a convenient value (e.g., 100) that represents a predetermined duration (e.g., 10 microseconds). Light controller 302 further includes a monostable multivibrator 840, which, in this embodiment, is adapted to output a pulse train of relatively constant amplitude and frequency. When register 820 is enabled (e.g., via an enable input) by a pulse from monostable multivibrator 840, register 820 is decremented or incremented depending on whether an output 812 (i.e., comparison signal 812) of comparator 810 is HIGH or LOW, respectively.

A pulse from monostable multivibrator 840 also causes the new value (i.e., the value produced by decrementing or incrementing a previous value) in register 820 to be loaded into a count-down timer 830 via a register output lines 822. A pulse from monostable multivibrator 840 also causes a counter output 832, of count-down timer 830, to go HIGH. Monostable multivibrator 840, which can be triggered by a clock or local oscillator (not shown), is set to operate at a convenient frequency, e.g., 2 kHz, that is much higher than the frequency of the signal of interest. When count-down timer 830 reaches zero, its counter output 842 returns to zero (i.e., LOW). Thus, the duration of each pulse is determined by the contents of the register 820 that were transferred to count-down timer 830. Each output pulse of counter output 832, which is delivered to light source 306 as light control signal 304, causes an optical pulse to be generated by light source 306 as transmitted light signal 308. One or ordinary skill in the art will appreciate that monostable multivibrator 840, in this embodiment, can be replaced by a clock or local oscillator that produces a signal having the desired frequence, e.g., 2 kHz.

In this embodiment, the modulation of light source 306 carries the plethysmography information, and the modulation of light source 306 is encoded in digital signals. Hence, no A/D conversion is necessary. The source modulation can be monitored in several different ways, some of which are discussed below. In each of these embodiments, it should be appreciated that the plethysmography information is obtained directly or indirectly from comparison signal 812.

In one embodiment (i.e., option 1), contents of register 820 are recorded, for example, by microprocessor or microcontroller 330 (shown in FIG. 3). According to the Nyquist theorem, register 820 need only be sampled at twice the highest frequency of the signal of interest. Sampling the register at 60–100 Hz is convenient. Other embodiments include digital logic that retains a maximum and/or a minimum value of register 820 over the duration of a cardiac cycle. At the end of the cardiac cycle, the maximum and/or minimum value(s) represent the arterial pulse amplitude, and are transferred to the microprocessor or microcontroller 330. Microprocessor 330 then analyzes and utilizes encoded information signal 328, as discussed above.

In another embodiment (i.e., option 2), comparison signal 812 is used as a digital output. Because comparator 810 is a high gain amplifier configured without negative feedback, its output will be either a LOW or HIGH signal. That it, it is essentially a digital signal. This is an implementation of a well-known sigma-delta modulation technique, which relies on oversampling a signal (e.g., comparison signal 712, in this embodiment) to the point where a low resolution quantizer produces a sufficient representation of the signal. Comparison signal 812 should be sampled at a relatively high rate, e.g., at the same rate of the LED pulse drive.

V. Adjust Number of LEDs Producing Light

Figure 9:
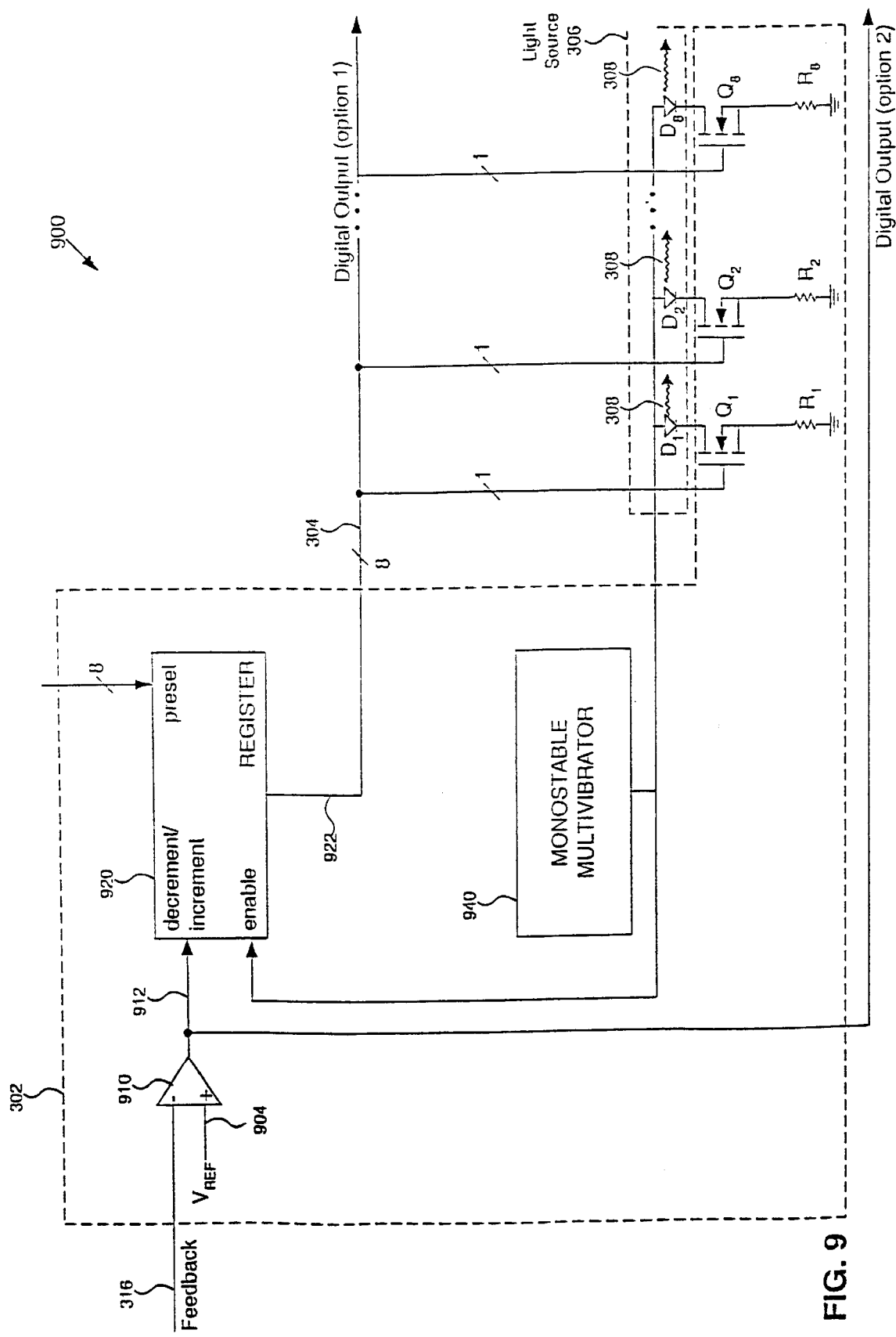
FIG. 9 illustrates a photoplethysmography device that selectively turns ON and OFF specific LEDs in an array of LEDs of a light source, according to an embodiment of the present invention.

According to another embodiment of the present invention, a pulse train having a fixed frequency and fixed pulse width is used to drive an array of LEDs (e.g., 8 LEDs) of a photoplethysmography device. The LEDs are independently turned ON or left OFF so that a relatively constant average light intensity is detected at a light detector of the device. FIG. 9 shows an exemplary block diagram of a device 900 that can be used to implement this embodiment of the present invention.

In this embodiment, light source 306 is pulsed with a fixed current and fixed frequency, but a control signal 304 controlling which LEDs are ON or OFF is adjusted such that a relatively constant average light intensity is detected by light detector 314. More specifically, a difference between feedback signal 316 (from light detector 314) and a reference signal is used to increase or decrease a digital signal that controls a plurality of parallel LEDs of light source 306 so that a relatively constant average light intensity is detected by light detector 314. Stated another way, light controller 306 adjusts a digital value of control signal 304 based on a difference between feedback signal 316 and a reference signal 904, such that a difference between feedback signal 316 and the reference signal is minimized.

In this embodiment, light controller 302 includes a comparator 910 that compares feedback signal 316 to fixed reference voltage signal 904 (e.g., 1.2 volts). Light controller 302 also includes a register 920 whose contents represent an intensity produced by light source 306, as shall be explained below. When register 920 is enabled (e.g., via an enable input) by a pulse from a monostable multivibrator 940, register 920 is decremented or incremented depending on whether an output 912 of comparator 910 is HIGH or LOW, respectively.

The LEDs (e.g., $D_1, D_2 \ldots D_8$) of light source 306 are placed physically close to one another (e.g., fabricated on the same substrate). The LEDs are independently turned ON or left OFF based on the arrival of a pulse from multivibrator 940. Multivibrator 940, which can be triggered by a clock or local oscillator (not shown), is set to operate at a convenient frequency (e.g., 2 kHz) significantly greater than the frequency content of the plethysmography information. Additionally, multivibrator 940 is set to produce pulses having a pulse width (e.g., 10 milliseconds) much smaller than the period of multivibrator 940. One or ordinary skill in the art will appreciate that monostable multivibrator 940, in this embodiment, can be replaced by a clock or local oscillator that produces a signal having the desired frequence, e.g., 2 kHz.

Whether the LEDs are turned ON or OFF is determined by register 920. More specifically, each bit (i) of register 920 is connected to a gate of a transistor ($Q_i$). Whether the gate is HIGH or LOW on the arrival of a pulse from the multivibrator 230 determines whether the corresponding LED ($D_i$) is turned ON (and emits light) or stays OFF. In a specific embodiment, each bias resistor ($R_i$) has a resistance approximately twice that of the previous bias resistor ($R_{i-1}$) such that its LED ($D_i$) emits twice as much light as the previous LED ($D_{i-1}$). In this way, the numerical value stored in register 920 is translated directly to the light intensity emitted by light source 306. For example, the resistance values can be adjusted so that the light intensity from a given LED ($D_i$), when measured at light detector 314, is twice that of the previous LED ($D_{i-1}$). In an alternative embodiment, the resistance of each resistor is approximately the same, providing for only N+1 different intensity states (e.g., 8+1=9 different intensity states), wherein N is the number of LEDs.

In these embodiments, the modulation of light source 306 carries the plethysmograph information, and the modulation of light source 306 is encoded in digital signals. Hence, no A/D conversion is necessary. The source modulation can be monitored in several different ways, some of which are discussed below. In each of these embodiments, it should be appreciated that the plethysmography information is obtained directly or indirectly from comparison signal 912.

The contents of the register 920 represents the intensity produced by light source 306. Contents of register 920 are recorded, for example, by a microprocessor or microcontroller 330 (shown in FIG. 3). According to the Nyquist theorem, register 920 need only be sampled at twice the highest frequency of the signal of interest. Sampling the register at 60–100 Hz is convenient. Other embodiments include digital logic that retains a maximum and/or a minimum value of register 920 over the duration of a cardiac cycle. At the end of the cardiac cycle, the maximum and/or minimum value(s) represent the arterial pulse amplitude, and are transferred to the microprocessor or microcontroller 330. Microprocessor 330 then analyzes and utilizes encoded information signal 328, as discussed above.

In another embodiment (i.e., option 2), comparison signal 912 may used as a digital output. Because comparator 910 is a high gain amplifier configured without negative feedback, its output will be either a LOW or HIGH signal. That it, it is essentially a digital signal. This is an implementation of a well-known sigma-delta modulation technique, which relies on oversampling a signal (e.g., comparison signal 712, in this embodiment) to the point where a low resolution quantizer produces a sufficient representation of the signal. Comparison signal 912 should be sampled at a relatively high rate, e.g., at the same rate of the LED pulse drive.

VI. Multiple Wavelengths

According to another embodiment of the present invention, light of more than one wavelength is transmitted from the light source. Such an embodiment can be useful, for example, in a pulse oximeter.

A pulse oximeter determines the percentage of hemoglobin that is saturated with oxygen using two wavelength spectrophotometry. A pulse oximeter typically includes an LED that transmits visible red light (e.g., 660 nm wavelength) and an LED that transmits infrared or near infrared radiation (e.g., 940 nm wavelength). In some devices, the LEDs are serially pulsed to produce an interleaved signal stream that is detected by a light sensor. The signal stream might consist of visible red light and infrared radiation, interleaved in any desired manner. The interleaved signal stream (i.e., light from the LEDs) is transmitted through or reflected from tissue of a patient and light is received by a light detector. As the light passes through and/or is reflected from tissue, some of the energy is absorbed by arterial and venous blood, tissue and the variable pulsations of arterial blood. Using electronic circuitry and/or software, the received signals in the infrared and red wavelengths are analyzed so that blood oxygenation levels (i.e., arterial oxygen saturation) can be determined. In other words, the light received by the light detector is used to produce the signals of interest in a typical pulse oximeter device.

As explained in U.S. Pat. No. 5,676,141 to Hollub, automated operation of pulse oximeters is quite complex because, for example, the received signal must be kept within the dynamic ranges of the elements (e.g., transistors and amplifiers) of the light detector. Otherwise signal clipping occurs and inaccurate measurements of blood oxygenation levels result. As will be explained below, the present invention overcomes many of the deficiencies of conventional devices by using the signal that modulates the light source (e.g., the light source includes a red LED and a near infrared LED) to derive plethysmography information. More specifically, the present invention avoids saturation by modulating the light source so that the light detector and related circuitry are maintained at or within an optimal operating point or range.

Figure 10A:
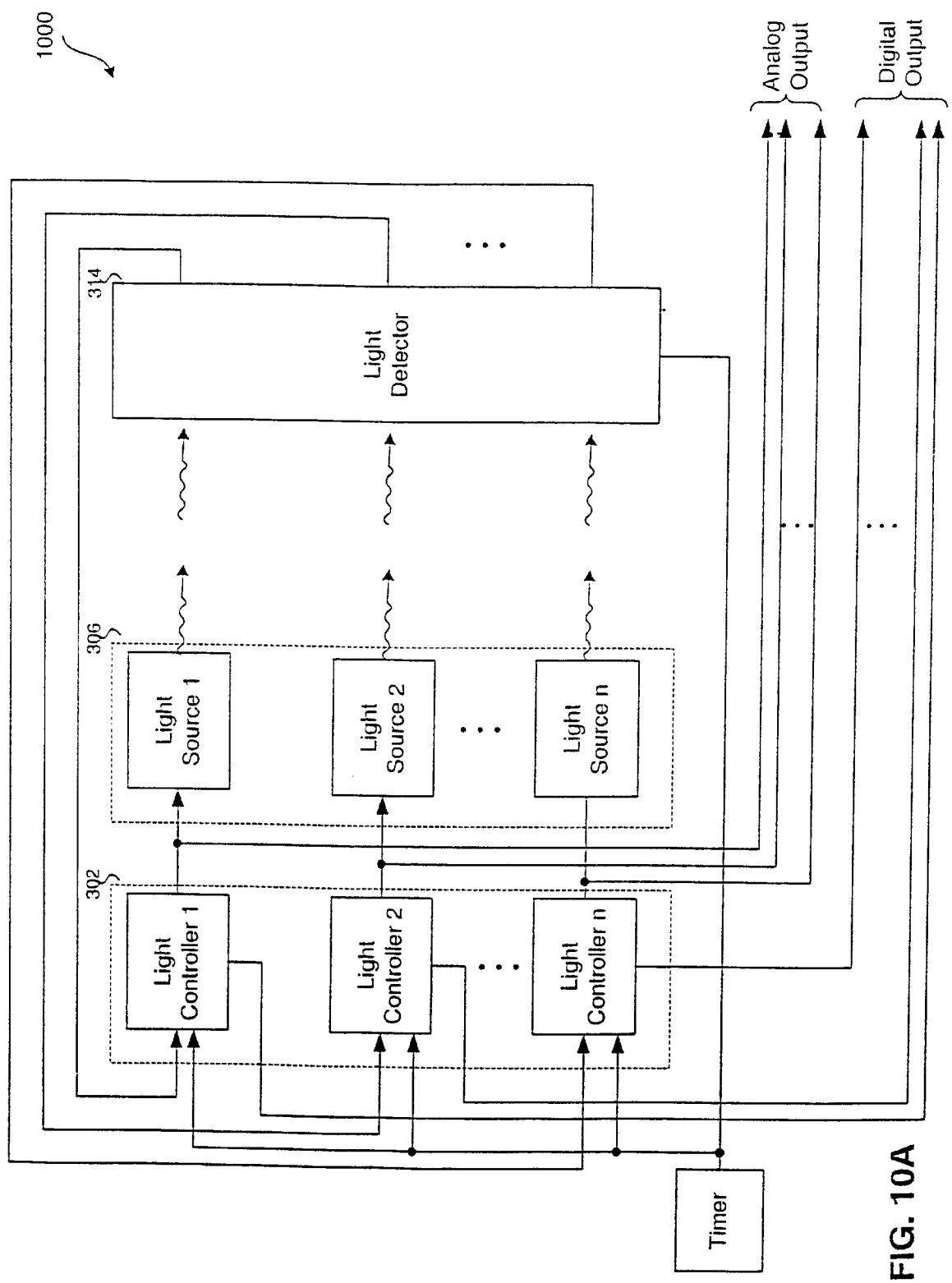
FIGS. 10A and 10B illustrate photoplethysmography devices that transmit and receive light of more than one wavelength.

FIG. 10A shows an exemplary block diagram of a device 1000 that can be used to transmit and receive light of more than one wavelength, according to an embodiment of the present invention. More specifically, FIG. 10 shows the high level architecture of a multiple wavelength plethysmography device 1000 that uses feedback control of source intensity. A time-division multiplexing scheme can be used, in which each light source is individually activated, with a possible time period of no illumination interposed between successive light source activations. Alternatively, a wavelength-division multiplexing scheme can be used, in which multiple sources are activated simultaneously but detected individually using multiple detectors and/or filters.

Figure 10B:
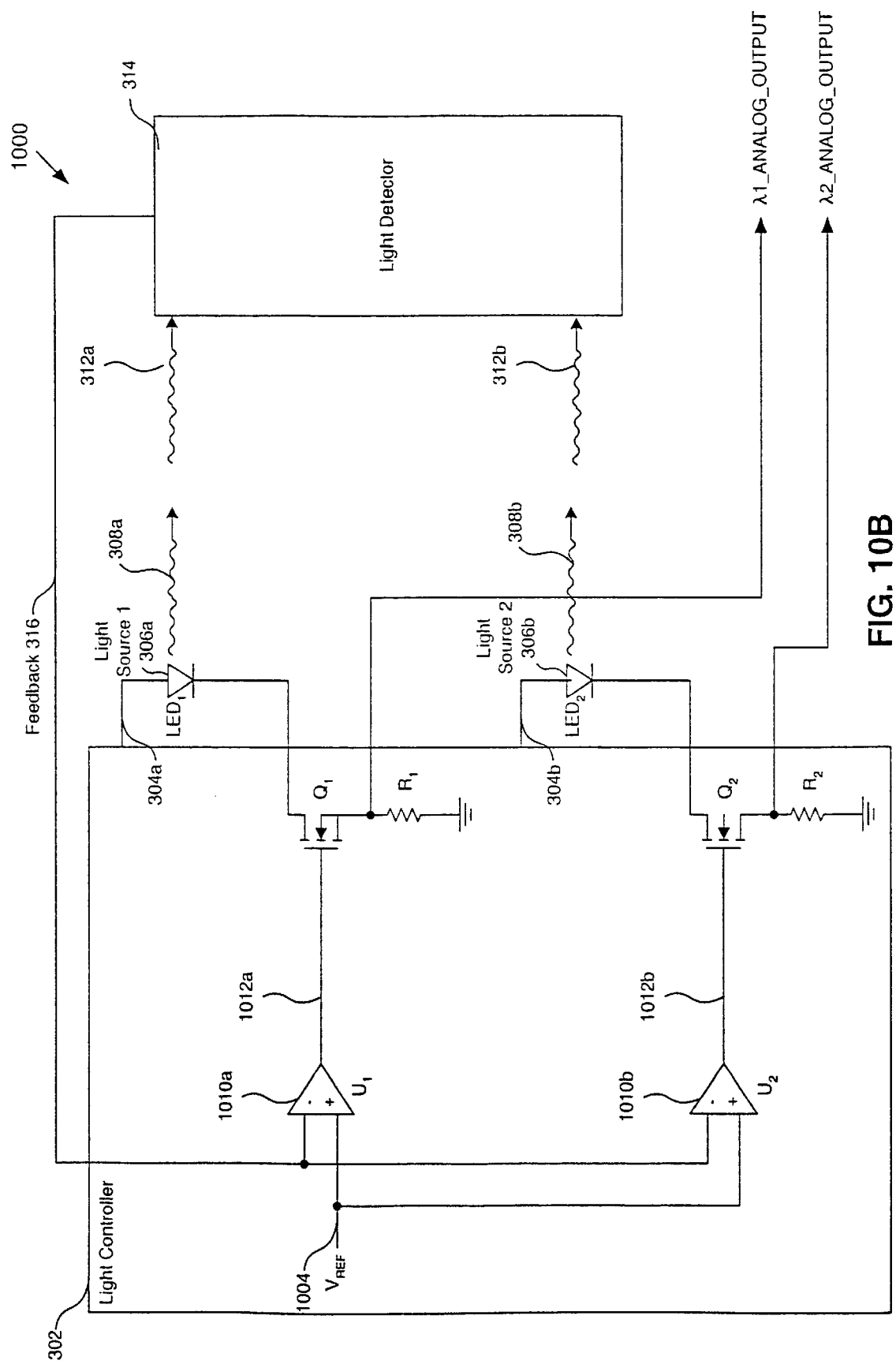
Figure 11:
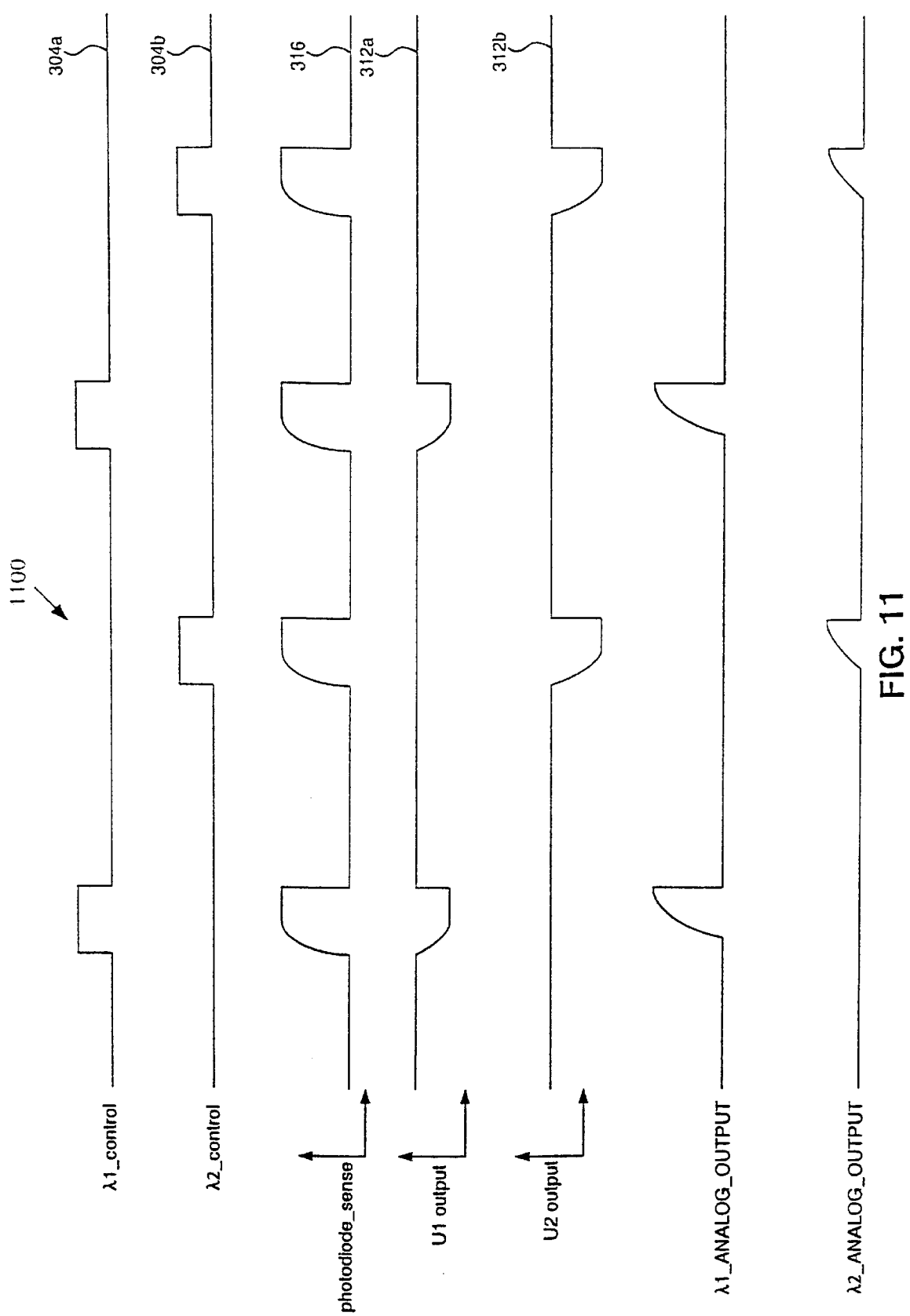
FIG. 11 illustrates a timing diagram that is useful in explaining operation of the device of FIG. 10B.

FIG. 10B illustrates a specific embodiment of device 1000 that uses feedback control of source intensity with two wavelengths. FIG. 11 illustrates a timing diagram 1100 that is useful in explaining operation of device 1000 of FIG. 10B.

Referring to FIGS. 10B and 11, in this embodiment, light controller 302 provides first light control signal 304a ($\lambda 1$_control) and second light control signal 304b ($\lambda 2$_control), respectively, to first light source 306a and second light source 306b. First light control signal 304a ($\lambda 1$_control) and second light control signal 304b ($\lambda 2$_control) include non-overlapping pulses, as illustrated in timing diagram 1100 of FIG. 11. This provides a time-division multiplexing embodiment.

Focusing on first light source 306a, when first light control signal 304 ($\lambda 1$_control) is off (or LOW), substantially no light of the first wavelength $\lambda 1$ is detected by light detector 314. This causes the voltage of the feedback signal 316 from light detector 314 to be substantially zero, in any case below reference voltage 1004 at the non-inverting input to a comparator 1010a (e.g., an op amp U). Thus, an output 1012a (also referred to as first comparison signal 1012a) of comparator 1010a will be HIGH, near the positive supply voltage, and transistor $Q_1$ will be strongly on. However, no current will flow through transistor $Q_1$ and $LED_1$ until first control signal 304a ($\lambda 1$_control) goes HIGH. At that point, current begins to flow through $LED_1$ producing a first transmit light signal 308a having a first wavelength $\lambda 1$. A first receive light signal 312a (having the first wavelength $\lambda 1$), received at light detector 314, causes feedback signal 316 (from light detector 314) to adjust (e.g., increase in voltage). Since feedback signal 316 is provided to the inverting input of comparator 1010a, comparator output 1012a (i.e., first comparison signal 1012a) begins to fall as the difference between its input voltage signals 316 and 1004 decreases. In response, transistor $Q_1$ becomes less strongly on. Before the end of the $\lambda 1$_control pulse of first light control signal 304a, the amount of generated light will reach an equilibrium. A current-sensing resistor $R_1$ converts the $LED_1$ current to a voltage signal ($\lambda 1$_ANALOG_OUTPUT) that is sampled or processed with filtering and amplification circuitry of analog signal processor 322. The plethysmography information in thus encoded in the analog signal derived from the source $LED_1$ current. A similar process occurs for second light source 306b, which includes $LED_2$ (which transmits a second light transmit signal 308b having a second wavelength $\lambda 2$).

Because first light control signal 304a ($\lambda 1$_control) and second light control signal 304b ($\lambda 2$_control) include non-overlapping pulses, as illustrated in timing diagram 1100 of FIG. 11, light detector 314 will only receive one of first receive light signal 312a (having the first wavelength $\lambda 1$) and second receive light signal 312b (having the second wavelength $\lambda 2$) at a time. Accordingly, as mentioned above, a time-division multiplexing embodiment is provided. The plethysmography information associated with the first wavelength $\lambda 1$ is encoded an analog signal derived from the source $LED_1$ current, and sensed using sense resistor $R_1$. The plethysmography information associated with the second wavelength $\lambda 2$ is encoded in an analog signal derived from the source $LED_2$ current, and sensed using sense resistor $R_2$. Exemplary $\lambda 1$_ANALOG_OUTPUT and λ2_ANALOG_OUTPUT are shown in timing diagram 1100. After these signals are processed by analog signal processor 322, and converted to digital signals 328 by A/D 326 (shown in FIG. 3), microprocessor 330 can analyze these signals.

According to an embodiment of the present invention, device 1000 is an oximeter device. More specifically, in one embodiment first light source 306a outputs a visible red light signal 308a (e.g., 660 nm wavelength), and second light source 306b outputs an infrared or near infrared light signal 308b (e.g., 940 nm wavelength). In this embodiment, $LED_1$ and $LED_2$ are serially pulsed to produce an interleaved signal stream that is detected by light detector 314. The signal stream consists of interleaved visible red light and infrared radiation. The interleaved signal stream is transmitted through or reflected from tissue of a patient and light is received by light detector 314. As the light passes through or is reflected from tissue, some of the energy is absorbed by arterial and venous blood, tissue and the variable pulsations of arterial blood. The plethysmography information signal associated with the red wavelength $\lambda 1$ is encoded in the analog signal ($\lambda 1$_ANALOG_OUTPUT) derived from the source $LED_1$ current. The plethysmography information associated with the infrared wavelength $\lambda 2$ is encoded in the analog signal ($\lambda 2$_ANALOG_OUTPUT) derived from the source $LED_2$ current. After conversion to digital signals 328, microprocessor 330 can calculate blood oxygenation levels based on these signals. It is noted that the term "light" refers to both visible and non-visible light, with light being further defined, when necessary, by specific wavelengths (e.g., visible red or infrared).

VII. Summary

Figure 12:
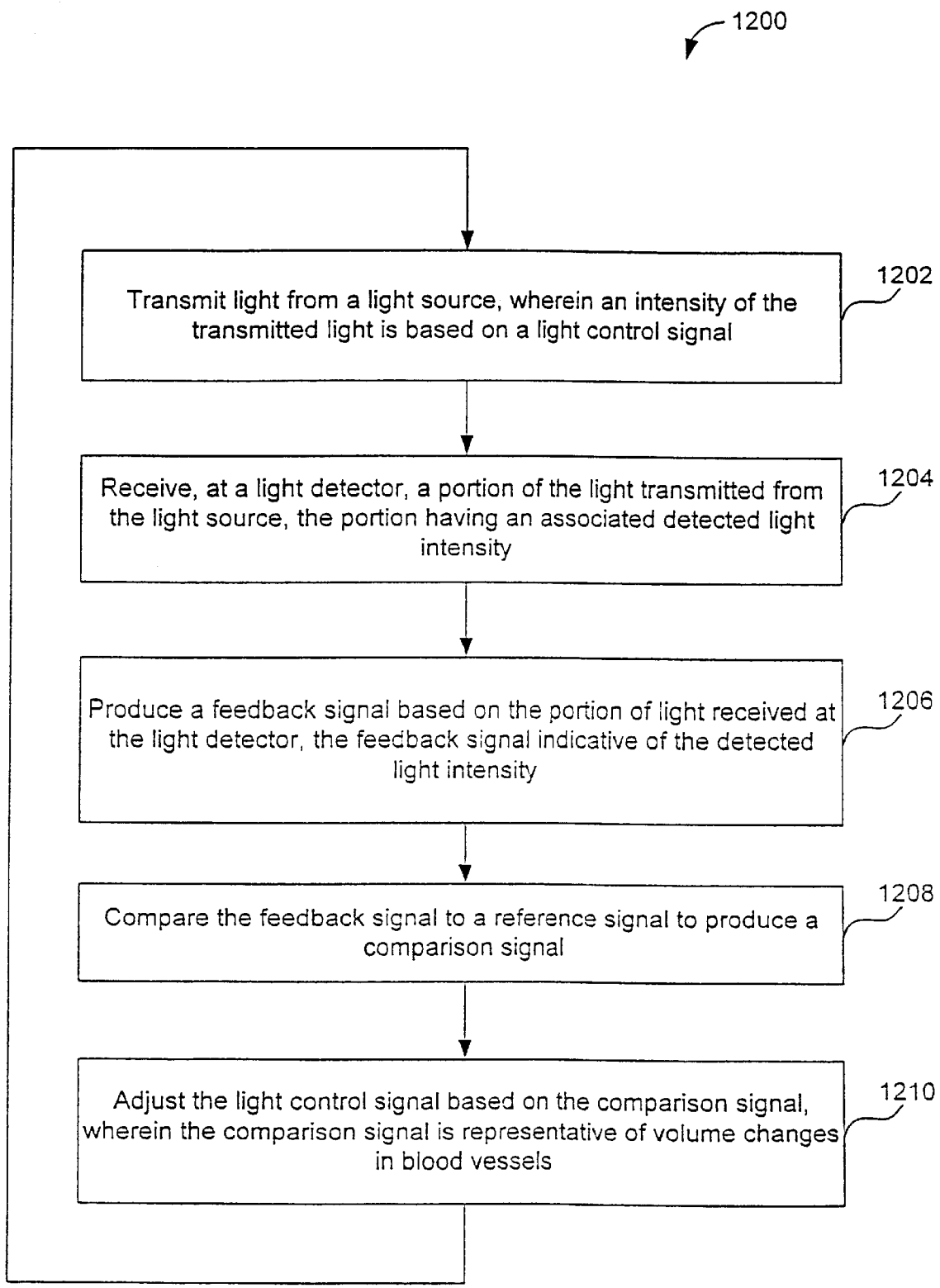
FIG. 12 is a flow diagram useful for describing an overview of the operation of embodiments of the present invention.

FIG. 12 is a flow diagram of a method 1200 that useful for describing an overview of the operation of embodiments of the present invention.

At a first step 1202, light is transmitted from a light source (e.g., light source 302) toward a capillary bed. The intensity of the transmitted light is based on a light control signal (e.g., light control signal 304).

Figure 1:
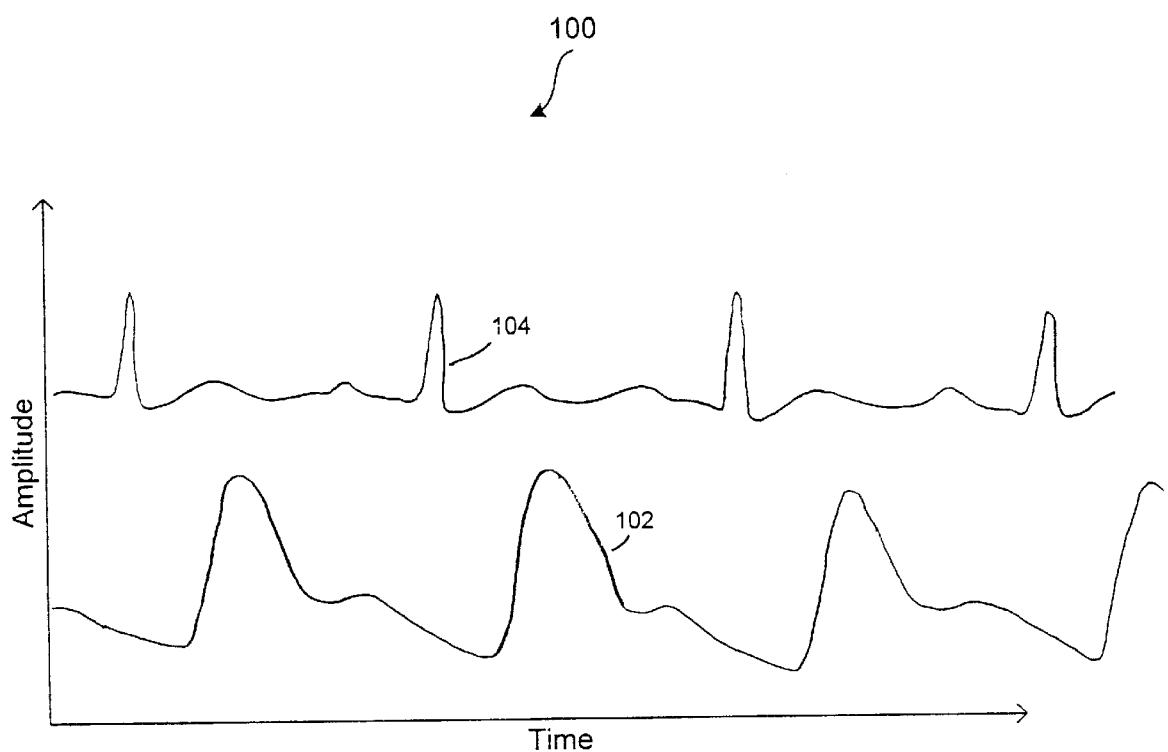
FIG. 1 illustrates an exemplary waveform produced by a plethysmography device.
Figure 2A:
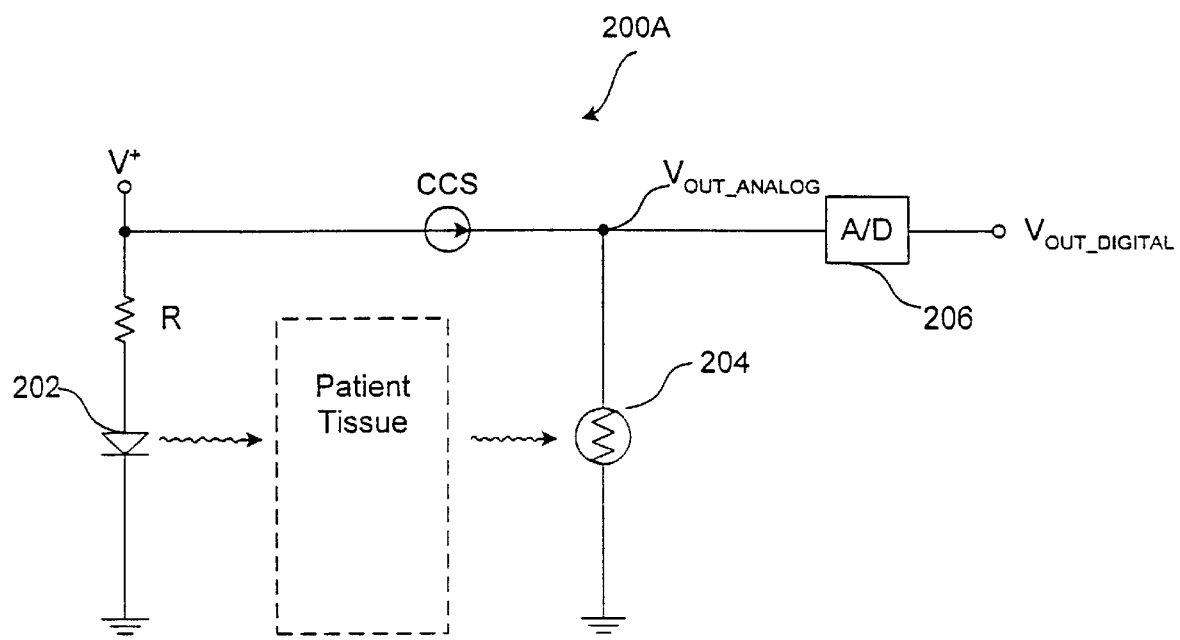
FIG. 2A is a simplified circuit diagram illustrating an exemplary conventional photoplethysmography device.
Figure 2B:
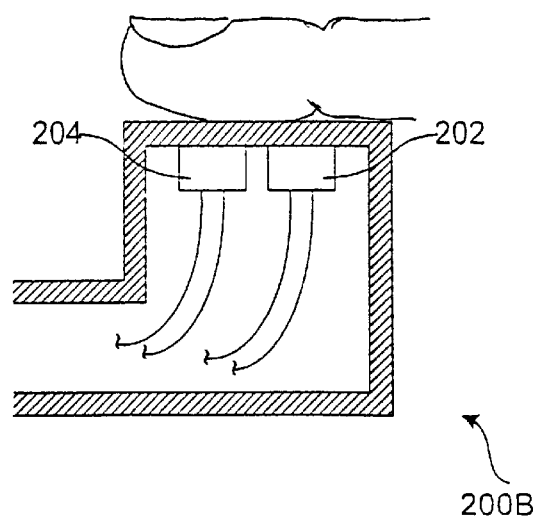
FIG. 2B is a simplified mechanical diagram illustrating a portion of an exemplary conventional photoplethysmography device.

At a next step 1204, a portion of the light transmitted from the light source is received at a light detector (e.g., light detector 314). The received portion of light, which was transmitted through a capillary bed (such as in an ear lobe or finger tip or some other patient tissue) prior to being received at the light detector, has an associated detected light intensity. The light source and light detector, which can be arranged in a transmission configuration or a reflection configuration, can be incorporated in an implantable device, or can be part of a conventional device (e.g., as shown in FIG. 1A).

At a next step 1206, a feedback signal (e.g., feedback signal 316) is produced based on the portion of light received at the light detector. The feedback signal is indicative of the detected light intensity.

Next, at a step 1208, the feedback signal is compared to a reference signal (e.g., using comparator 610, 710, 810, 910 or 1010) to produce a comparison signal (e.g., comparison signal 610, 710. 810, 910 or 1010), which is representative of volume changes in blood vessels.

Then, at a step 1210, the light control signal (e.g., light control signal 304) is adjusted based on the comparison signal. The light control signal is thus also representative of volume changes in blood vessels. For example, the comparison signal can be used to adjust the amplitude of the light control signal. Alternatively or additionally, the comparison signal can be used to adjust the frequency of the light control signal. Alternatively or additionally, the comparison signal can be used to adjust pulse widths of the light control signal. Alternatively or additionally, the comparison signal can be used to control which LEDs, of an LED array, are turned ON or OFF.

Thus, the comparison signal, which is representative of volume changes in blood vessels, is used to modulate the intensity of the light transmitted from the light source. Accordingly, over time, plethysmography information (which represents volume changes in blood vessels) is obtained directly or indirectly from the comparison signal. In each of the embodiments the light control signal e.g., light control signal 304) is also representative of volume changes in blood vessels. Thus, plethysmography information can also (or alternatively) be obtained directly or indirectly from the light control signal.

Steps 1202 through 1210 can be continually or frequently (i.e., more than once per heart beat) performed such that the light control signal, and thus the intensity of the transmitted light, is adjusted more than once per heart beat. In one embodiment, steps 1202 through 1210 are performed such that the light controls signal, and thus the transmitted light, is adjusted more than twenty times per heart beat.

Such plethysmography information, and thus the present invention, can be used in a variety of ways. For example, the present invention can be used to monitor pulse rate. The present invention can also be used for arrhythmia discrimination, capture verification, and/or electrical sensing optimization and noise rejection. The present invention can also be used to monitor the autonomic nervous system, as with diabetic patients or heart failure patients. The present invention can also be used to monitor respiration, as with heart failure and obstructive sleep apnea patients. As specifically described above, the present invention can also be used to measure blood oxygenation levels.

Further, the present invention can be used to measure arterial pulse amplitude, which can in turn be used to optimize cardiac pacing parameters. Examples of systems and methods that use arterial pulse amplitudes to optimize pacing parameters are provided in U.S. patent application Ser. No. 09/759,305, entitled "Methods, Systems and Devices for Optimizing Cardiac Pacing Parameters," filed Jan. 12, 2001, and in U.S. patent application Ser. No. 09/780,735, entitled "Methods, Systems and Devices for Optimizing Cardiac Pacing Parameters Using Evolutionary Algorithms", filed Feb. 9, 2001, both of which have been incorporated by reference above. The methods and devices of the present invention can be used to measure arterial pulse amplitudes that are used to optimize cardiac pacing parameters in accordance with the above described patent applications, and in accordance with any known and/or future developed methods, systems, and devices that optimize cardiac pacing parameters based on measures of arterial pulse amplitude and/or other plethysmography information.

The photoplethysmography devices of the present invention may operate in either a transmission configuration or a reflection configuration. In the transmission configuration, light source 302 and light detector 304 may face one another and a segment of the body (e.g., a finger or earlobe) is interposed between the source and detector. In the reflection configuration, light source 302 and light detector 304 are mounted adjacent to one another, e.g., on the surface of the body. The photoplethysmography devices of the present invention can also be incorporated into an implantable cardioverter defibrillator (ICD) or pacemaker, and thus implanted. In such embodiments, light source 302 and light detector 304 can be mounted adjacent to one another on the housing (e.g., can) or header of the ICD, as disclosed in U.S. patent application Ser. No. 09/543,214, entitled "Extravascular Hemodynamic Sensor", filed Apr. 5, 2000, which was incorporated by reference above. The photoplethysmography devices of the present invention can alternatively be incorporated into non-stimulation implantable devices whose main purpose is to monitor hemodynamic function. The housing of an implantable ICD or any other implatable device can include an optically transparent window. In such embodiments, light source 302 and light detector 304 can be located within the housing and arranged such that transmitted and detected light are transmitted and detected through the window.

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

What is claimed is:

1. For use in a medical device including a light source and a light detector, a method for monitoring volume changes in blood vessels, comprising the following steps:
   (a) transmitting light from the light source, wherein an intensity of the transmitted light is based on a light control signal;
   (b) receiving, at the light detector, a portion of the light transmitted from the light source, the portion having an associated detected light intensity;
   (c) producing a feedback signal based on the portion of light received at the light detector, the feedback signal indicative of the detected light intensity;
   (d) comparing the feedback signal to a reference signal to produce a comparison signal; and
   (e) adjusting the light control signal based on the comparison signal,
       wherein at least one of the comparison signal and the light control signal is representative of volume changes in blood vessels.

2. The method of claim 1, further comprising the steps of:
   converting the comparison signal from a voltage signal to a current signal, the light control signal comprising the current signal; and
   driving the light source based on the current signal.

3. The method of claim 2, further comprising the steps of:
   producing a further voltage signal that is proportional to the current signal, the further voltage signal representative of volume changes in blood vessels; and
   measuring the further voltage signal to thereby monitor volume changes in blood vessels.

4. The method of claim 1, wherein step (e) comprises adjusting the light control signal to thereby keep the detected light intensity of the portion of light received at the light detector relatively constant.

5. The method of claim 4, wherein step (e) comprises adjusting an amplitude of the light control signal to thereby keep the detected light intensity of the portion of light received at the light detector relatively constant.

6. The method of claim 4, wherein step (e) comprises adjusting a frequency of the light control signal to thereby keep the detected light intensity of the portion of light received at the light detector relatively constant.

7. The method of claim 4, wherein step (e) comprises adjusting pulse widths of the light control signal to thereby keep the detected light intensity of the portion of light received at the light detector relatively constant.

8. The method of claim 1, wherein step (e) comprises adjusting the light control signal to minimize a difference between the feedback signal and the reference signal.

9. The method of claim 8, wherein step (e) comprises adjusting an amplitude of the light control signal to minimize a difference between the feedback signal and the reference signal.

10. The method of claim 8, wherein step (e) comprises adjusting a frequency of the light control signal to minimize a difference between the feedback signal and the reference signal.

11. The method of claim 8, wherein step (e) comprises adjusting a pulse width of the light control signal to minimize a difference between the feedback signal and the reference signal.

12. The method of claim 1, wherein step (c) comprises the steps of:
   (c.1) adjusting a current signal based on the portion of light received at the light detector; and
   (c.2) converting the current signal to a voltage signal, wherein the feedback signal comprises the voltage signal.

13. The method of claim 1, wherein:
   the light control signal comprises a digital signal; and
   the light source comprises a plurality of LEDs, each of which is turned on or off based on the digital signal.

14. The method of claim 13, wherein step (e) comprises adjusting the digital signal to minimize a difference between the feedback signal and the reference signal.

15. The method of claim 13, wherein step (e) comprises adjusting the digital signal to thereby keep the detected light intensity of the portion of light received at the light source relatively constant.

16. For use in a medical device including a light detector and a light source that transmits light of at least two different wavelengths, a method for monitoring volume changes in blood vessels, comprising the following steps:
   (a) transmitting light having a first wavelength and light having a second wavelength from the light source, wherein an intensity of the transmitted light is based on a first light control signal and a second light control signal;
   (b) receiving, at the light detector, a portion of the light having the first wavelength and a portion of the light having the second wavelength transmitted from the light source, each portion having an associated detected light intensity;
   (c) producing a first feedback signal based on the portion of light having the first wavelength, and a second feedback signal based on the portion of light having the second wavelength, each feedback signal indicative of the associated detected light intensity;
   (d) comparing the first feedback signal to a reference signal to produce a first comparison signal, and the second feedback signal to a reference signal to produce a second comparison signal; and
   (e) adjusting the first and second light control signals, respectively, based on the first and second comparison signals,
       wherein the first and second comparison signals are representative of volume changes in blood vessels.

17. The method of claim 16, wherein the first wavelength is within the red visible light spectrum, and the second wavelength is within the infrared or near infrared light spectrum.

18. The method of claim 17, further comprising the step of:

(g) producing first and second plethysmography information signals that are respectively proportional to the transmitted light having the first wavelength and the transmitted light having the second wavelength; and (h) calculating blood oxygenation levels based on the first and second plethysmography information signals.

19. A device for monitoring volume changes in blood vessels, comprising:

a light controller to produce a light control signal;

a light source to transmit light based on the light control signal, wherein an intensity of the transmitted light is based on the light control signal;

a light detector to receive a portion of the light transmitted from the light source, the portion having an associated detected light intensity, and produce a feedback signal based on the portion of light received at the light detector, the feedback signal indicative of the detected light intensity; and a comparator to compare the feedback signal to a reference signal to produce a comparison signal, wherein the light controller adjusts the light control signal based on the comparison signal, at least one of the comparison signal and the light control signal being representative of volume changes in blood vessels.

20. The device of claim 19, further comprising a transistor to convert the comparison signal from a voltage signal to a current signal that drives the light source, wherein the light control signal comprises the current signal.

21. The device of claim 20, further comprising a resistor to produce a further voltage signal proportional to the current signal, wherein the further voltage signal is representative of volume changes in blood vessels.

22. The device of claim 19, wherein the light controller adjusts an amplitude of light control signal based on the comparison signal.

23. The device of claim 19, wherein the light control signal comprises a pulse train, and wherein the light controller adjusts a frequency of the pulse train based on the comparison signal.

24. The device of claim 19, wherein the light controller further comprises:

a monostable multivibrator (MMV);

a register to store a value and increment or decrement the value based on the comparison signal when the register receives a pulse from the MMV;

a countdown timer to receive the value stored in the register when the countdown timer receives a pulse from the MMV, and to output a trigger pulse after counting from the value down to zero, wherein the MMV produces a pulse having a substantially constant amplitude and pulse width when the MMV receives a trigger pulse from the countdown timer, and wherein the MMV produces a plurality of the pulses having substantially constant amplitude and pulse width, the plurality of the pulses having a variable frequency based on the comparison signal, wherein the light control signal comprises the plurality of pulses having the variable frequency.

25. The device of claim 24, wherein the countdown timer receives a plurality of values from the register over time, the plurality of values representative of volume changes in blood vessels.

26. The device of claim 19, wherein the light control signal comprises a pulse train, and wherein the light controller adjusts pulse widths of the pulse train based on the comparison signal.

27. The device of claim 19, wherein the light controller adjusts the light control signal more than once per heart beat.

28. The device of claim 19, wherein the light controller further comprises:

a pulse means for producing a train of trigger pulses having a substantially constant frequency;

a comparator that compares the feedback signal to a reference signal to produce a comparison signal;

a register to store a value and increment or decrement the value based on the comparison signal when the register receives a trigger pulse from the pulse means; and a countdown timer to receive the value stored in the register when the countdown timer receives a trigger pulse from the pulse means, wherein the count down timer outputs a pulse after counting from the value down to zero, the countdown timer thereby producing a plurality of pulses each having a pulse width proportional to the comparison signal.

29. The device of claim 28, wherein the countdown timer receives a plurality of values from the register over time, the plurality of values representative of volume changes in blood vessels.

30. The device of claim 19, wherein:

the light control signal comprises a digital signal; and the light source comprises a plurality of LEDs, each of which is turned on or off based on the digital signal.

31. The device of claim 19, wherein the light source comprises a plurality of LEDs, and wherein the light controller further comprises:

a pulse means for producing a train of trigger pulses having a substantially constant frequency;

a register to increment or decrement a stored value based on the comparison signal when the register receives a trigger pulse from the pulse means;

wherein the register outputs the value as a digital signal when the enable pin is activated by a trigger pulse of the pulse means; and wherein each of the plurality of LEDs is independently turned on or off based on the digital signal when the LEDs receive a trigger pulse from the pulse means.

32. The device of claim 19, wherein the light source and the light detector are arranged in a transmission configuration.

33. The device of claim 32, wherein the light source and the light detector are arranged such that a human appendage can be placed between the light source and the light detector.

34. The device of claim 19, wherein the light source and the light detector are arranged in a reflection configuration.

35. The device of claim 34, wherein the light source and the light detector are located relatively adjacent to one another.

36. The device of claim 35, wherein the light source and the light detector are arranged such that a human appendage can be placed upon the light source and the light detector.

37. The device of claim 35, wherein the light source, the light controller, and the light detector are incorporated into an implantable device.

38. The device of claim 19, further comprising:

a means for determining volume changes in blood vessels based on at least one of the comparison signal and the light control signal.

39. A device for monitoring volume changes in blood vessels, comprising:
- a light controller to produce a light control signal based on a first light control signal and a second light control signal;
- a light source to transmit light having a first wavelength and light having a second wavelength based on the light control signal, wherein an intensity of the transmitted light is based on the first and second light control signals;
- a light detector to
  - receive a portion of the light having the first wavelength and a portion of the light having the second wavelength transmitted from the light source, each portion having an associated detected light intensity, and
  - produce a first feedback signal based on the portion of light having the first wavelength and a second feedback signal based on the portion of the light having the second wavelength, each feedback signal indicative of the associated detected light intensity;
- a first comparator to compare the first feedback signal to a reference signal to produce a first comparison signal; and
- a second comparator to compare the second feedback signal to a reference signal to produce a second comparison signal,
- wherein the light controller adjusts the light control signal based on the first and second comparison signals, the first and second comparison signals being representative of volume changes in blood vessels.

40. The device of claim 39, wherein the light sources comprises:
- a first light emitting diode (LED) that transmits the light having the first wavelength; and
- a second LED that transmits the light having the second wavelength.

41. The device of claim 40, wherein the first wavelength is within the red visible light spectrum, and the second wavelength is within the infrared or near infrared light spectrum.

42. The device of claim 41, further comprising:
- means for producing first and second plethysmography information signals that are respectively proportional to the transmitted light having the first wavelength and the transmitted light having the second wavelength; and
- means for calculating blood oxygenation levels based on the first and second plethysmography information signals.

43. An implantable device for monitoring volume changes in blood vessels, comprising:
- a light source to transmit light;
- a light detector to receive a portion of the light transmitted from the light source, the portion having an associated detected light intensity;
- a light controller to adjust an intensity of the transmitted light based on the detected light intensity; and
- a means for determining volume changes in blood vessels based on a signal produced by the light controller, the signal being proportional to the intensity of the transmitted light.

44. The device of claim 43, wherein the light source and the light detector are located adjacent to one another on the housing of the implantable device.

45. The device of claim 43, wherein the light source and the light detector are located adjacent to one another on the header of the implantable device.

46. The device of claim 43, wherein the implatable device includes a housing having an optically transparent window, and wherein the light source and the light detector are located adjacent to one another within the housing such that the transmitted light is directed through the window and the received portion of the transmitted light is received through the window.

47. The device of claim 43, wherein the means for determining determines volume changes in blood vessels more than once per heart beat.

48. The device of claim 43, wherein the means for determining determines volume changes in blood vessels at least twenty times per heart beat.

* * * * *